United States Patent
Juncker et al.

(10) Patent No.: US 11,648,555 B2
(45) Date of Patent: May 16, 2023

(54) DOMINO CAPILLARY MICROFLUIDIC CIRCUIT

(71) Applicant: THE ROYAL INSTITUTION FOR THE ADVANCEMENT OF LEARNING/MCGILL UNIVERSITY, Montréal (CA)

(72) Inventors: David Juncker, Verdun (CA); Ayokunle Olanrewaju, Montreal (CA); Mohamed Yafia Okba Salem, Montreal (CA)

(73) Assignee: THE ROYAL INSTITUTION FOR THE ADVANCEMENT OF LEARNING/MCGILL UNIVERSITY, Montreal (CA)

( * ) Notice: Subject to any disclaimer, the term of this patent is extended or adjusted under 35 U.S.C. 154(b) by 389 days.

(21) Appl. No.: 16/757,915

(22) PCT Filed: Oct. 19, 2018

(86) PCT No.: PCT/CA2018/051322
§ 371 (c)(1),
(2) Date: Apr. 21, 2020

(87) PCT Pub. No.: WO2019/075573
PCT Pub. Date: Apr. 25, 2019

(65) Prior Publication Data
US 2020/0346211 A1    Nov. 5, 2020

Related U.S. Application Data

(60) Provisional application No. 62/575,418, filed on Oct. 21, 2017.

(51) Int. Cl.
*B01L 3/00*       (2006.01)
*B01F 23/45*      (2022.01)
(Continued)

(52) U.S. Cl.
CPC .......... *B01L 3/50273* (2013.01); *B01F 23/45* (2022.01); *B01F 23/49* (2022.01);
(Continued)

(58) Field of Classification Search
CPC .............. B01L 3/50273; B01L 3/5027; B01L 2400/0406; B01L 2400/0688; B01F 25/4331; B01F 33/3017
See application file for complete search history.

(56) References Cited

U.S. PATENT DOCUMENTS 10,166,541 B2 *    1/2019   Kulinsky ............. B01D 21/262
2012/0241035 A1    9/2012   Shih et al.

FOREIGN PATENT DOCUMENTS

WO    2013029159    3/2013

OTHER PUBLICATIONS

International search Report and written opinion dated Jan. 18, 2019 for Application PCT/CA/2018/051322.

* cited by examiner

*Primary Examiner* — Brian J. Sines
(74) *Attorney, Agent, or Firm* — Norton Rose Fulbright Canada (57) ABSTRACT

There is disclosed a capillary microfluidic circuit including a main channel communicating with a flow inducing element. The main channel has intermediary inlets. Reservoirs for containing one or more liquids prior to being drawn into the main channel. The reservoirs include a first reservoir and at least a second reservoir. Each of the reservoirs has an upstream end connectable to vents for filling the reservoirs with the one or more liquids and a downstream end. The downstream end of each of the reservoirs is connected to the intermediary inlets of the main channel A conduit is disposed between the first reservoir and the a least a second reservoir. The conduit links the downstream end of the first (Continued)

reservoir with the upstream end of the at least a second reservoir.

15 Claims, 9 Drawing Sheets

(51) Int. Cl.
  *B01F 23/40* (2022.01)
  *B01F 25/433* (2022.01)
  *B01F 33/301* (2022.01)
  *B01F 101/23* (2022.01)

(52) U.S. Cl.
  CPC ...... *B01F 25/4331* (2022.01); *B01F 33/3017* (2022.01); *B01L 3/502738* (2013.01); *B01F 2101/23* (2022.01); *B01L 2300/0816* (2013.01); *B01L 2300/0864* (2013.01); *B01L 2300/12* (2013.01); *B01L 2300/161* (2013.01); *B01L 2400/0406* (2013.01); *B01L 2400/0487* (2013.01); *B01L 2400/0688* (2013.01)

DOMINO CAPILLARY MICROFLUIDIC CIRCUIT

TECHNICAL FIELD

The application relates generally to micro fluidic systems and, more particularly, to capillarics.

BACKGROUND

Capillarics or capillary microfluidic circuits (CCs) are able to move liquids in complex pre-programmed sequences relying entirely on capillary forces for pumping and valving. Capillary forces are created by the surface tension between a liquid and a container. A capillary action is the ability of a liquid to flow without assistance of external forces. Capillaric circuits may be used for bacterial detection. However, capillaric circuits might allow up to eight sequential liquid delivery operations thanks to retention burst valves that each "burst" at a predefined pressure. However, the number of sequential steps cannot be scaled up because of limitations in fabrication resolution and aspect-ratio constraints, reproducibility, and variability in the surface tensions of different reagents, and constraints of the pressure within the circuit during fluidic operations that might lead to wrong sequences.

Current CCs are known to be composed of individual capillaric fluidic elements including capillary pumps, trigger valves, retention valves (RVs), and retention burst valves (RBV). In certain designs, these elements are designed and arranged in the circuit such that sequential liquid delivery by RBVs is possible, wherein each valve "bursts" at a predefined pressure encoded by the valve surface chemistry and geometry.

Previous designs of capillarics may be susceptible to differences in the surface tension of liquid placed within each valve. When there are variations in the surface tension of liquid, this might translate into differences in the capillary pressures of the valves and could result in deviations from the expected flow sequence. Existing capillaric designs can also be susceptible to imprecisions in the microfabrication of RBVs, as small differences in geometry can lead to different burst pressures and lead to an incorrect sequence of liquid delivery. Hence there is a need to ensure that the pressure difference between RBV is sufficiently high to prevent sequence errors. However, this may limit the number of liquids that can be delivered sequentially, as the dimensions are limited. One requirement is that the capillary pump has a higher pressure than the strongest RBV, which limits the lower size of structures that can be made. The weakest RBV cannot exceed beyond the regime of capillary phenomena, limiting the smallest dimension of the cross-section of the RBV to below about 1 cm.

Additional challenges have also been encountered with existing capillaric circuits. Previous designs of capillaric circuits have had to consider the pressure within the circuit during drainage of an RBV, the reservoir attached to an RBV, or flow in any other section of the circuit, and ensure that the pressure at each non-burst RBV remained below its burst pressure while these fluidic operations proceeded. If such conditions are not satisfied, the order or drainage may not follow the desired order. This imposes constraints on the overall architecture and design of the circuits, and can limit the functionality that can be designed.

Previous designs of capillarics are also difficult to scale, and often can only accommodate a limited number of sequential drainage steps because of the requirements of differences between the burst pressure of different RBVs, and because of the requirements of not exceeding the pressure of all non-burst RBVs during any other fluidic operation.

SUMMARY

There is disclosed herein domino capillaric circuits (DCCs) designed to provide simple and scalable pre-programmed liquid delivery. DCCs control sequential liquid delivery using a domino effect where reservoirs are opened to air and able to drain only after the preceding reservoir has completely drained. DCCs can also be used to implement simultaneous liquid delivery by triggering two reservoirs at once, akin to one domino hitting two dominos. The DCCs for sequential liquid delivery might be scaled up by adding another trigger unit, like a line of falling dominos that can be extended by adding any number of additional dominos.

A DCC as described herein can also comprise hydrophilic conduits spontaneously filling by capillary force, reservoirs, trigger valves, retention valves, retention burst valves and a capillary pump. In addition, the present DCCs comprise at least one microchannel that acts as pneumatic air conduit and that connect two hydrophilic conduits, serially linking a downstream end of a reservoir to an upstream end of the next reservoir. After drainage of the first reservoir, the second reservoir is connected to air and can be drained. A third reservoir can be added to the circuit and serially connected by an air conduit, so that it only drains after drainage of the second one, and so on, which is the domino effect. The reservoir cannot drain as long as the preceding reservoir is not completely drained. This permits the number of autonomous liquid delivery steps in the circuits to be increased. For example, the number of autonomous liquid delivery steps may be increased from eight to sixteen, or alternately to as much as (or more than) ninety-six, with the capability to scale it up even further simply by adding more reservoirs and air conduits that may be identical in geometry.

In one particular embodiment, the DCC is formed of only one layer, wherein the capillary channels within this layer are filled by flow connected by conduit links that are filled by air. In this embodiment, the filling of the capillary channels can be prevented by using capillary elements including trigger valves.

In one particular embodiment, the DCCs comprise two layers: a hydrophilic hydraulic layer and a hydrophobic pneumatic layer. The hydrophilic layer includes reservoirs, trigger valves, retention valves, retention burst valves, inlets, vents, and a capillary pump. The hydrophobic pneumatic layer includes microchannels that act as air conduits serially linking a downstream end of a reservoir to an upstream end of the next reservoir. After drainage of the first reservoir, the second reservoir is connected to air and can be drained, and then the third, and so on, which is the domino effect. The second reservoir cannot drain as long as the first reservoir is not completely drained. This might allow increasing the number of autonomous liquid delivery steps demonstrated in circuits from eight to sixteen, for example only, and may permit the number of autonomous liquid delivery steps to be increased up to ninety-six with the capability to scale it up even further simply by adding more air conduits that may be identical in geometry.

In this embodiment, wherein the DCC is formed as a two layer system, the filling of the capillary channels can be prevented by using hydrophobic coating applied to one or more of the conduits of the DCC.

DCCs can also be made with a one layer construction, comprising a hydrophilic hydraulic circuit and a hydrophobic pneumatic layer that prevent liquids from filling it while defining an air trap between two reservoirs, and thus establishing an air connection. The hydrophilic layer includes reservoirs, trigger valves, retention valves, retention burst valves, inlets, vents, and a capillary pump. When the reservoirs are filled, the hydrophobic pneumatic layer is not filled and thus acts as an air conduit. The air conduits are designed so as to serially link a downstream end of a reservoir to an upstream end of the next reservoir. After drainage of the first reservoir, the second reservoir is connected to air and can be drained, and then the third, and so on, which is the domino effect. The second reservoir cannot drain as long as the first reservoir is not completely drained. This might allow increasing the number of autonomous liquid delivery steps demonstrated in circuits from eight to sixteen, for example only, and may and may permit the number of autonomous liquid delivery steps to be increased to ninety-six, with the capability to scale it up even further simply by adding more air conduits that may be identical in geometry.

The two-layer structure with the hydrophilic hydraulic layer and the hydrophobic pneumatic layer that might enable the use of air vents for pre-programmed liquid delivery. This architecture might enable the cover to be easily reconfigured for sequential drainage or simultaneous drainage of liquids from reagent reservoirs.

CCs are the gold standard in liquid delivery using capillary forces. They have retention valves and retention burst valves (RBVs) that enable sequential liquid delivery according to capillary pressures encoded by the height and width of microchannels in the CC. This allows the use of CCs to automate liquid delivery processes that may be applied for biochemical applications, for example rapid detection of bacteria. DCCs distinguish themselves from the CCs by removing the critical dependency on having a unique RBV for each liquid delivery step. DCCs require only one RBV upstream of the first reservoir, whereas all reservoirs are linked to a RV. As such, only two RBV sizes can be used to design a DCC with 8, 16, 32, or 96 liquid delivery steps. This might ease the scaling up the number of liquid delivery steps in capillary microfluidics.

DCCs might offer a high degree of control over reservoir drainage time and sequence. It would have been difficult to obtain the number of autonomous liquid delivery steps programmed herein in the past with traditional CCs.

DCCs can be simple to fabricate and easy to use. They can be preprogrammed for sequential and simultaneous liquid delivery. DCCs can readily be scaled up and are less sensitive to surface tension variations between liquids, and hence may find numerous applications in research, clinic or industry.

However, once the liquid flow starts in capillaric systems it cannot be stopped since the capillary pump will continuously keep draining the liquid. Hence, all the capillary microfluidic systems so far are continuous flow systems.

It is introduced an autonomous capillary circuit with a pre-programmed valving system using sacrificial reservoir that is able to stop a flow of a sample contained within a reservoir, drain while the sample is stopped, and resumes the flow of the sample after the sacrificial reservoir is drained.

The sacrificial reservoir volume and flow rate may act as a programmable timer that stops and restores the flow of the sample after the sacrificial reservoir was emptied. The sacrificial reservoir may drain to a location that is closer to the pump to stop the sample drainage.

The sacrificial reservoirs can be also used to position a sample at a specific location on the chip. The sample positioning occurs using the liquid inside the sacrificial reservoir which displaces and pushes the sample to a specific location based on the sacrificial reservoir volume. This valving system might be able to perform more complex operations in capillaric circuits and can mimic the active microfluidics valving system.

There is also disclosed a chip that might be able to analyse blood coagulation disorders. More specifically, the chip might be able to analyse the blood coagulation process and to determine the peak time for thrombin generation. Hemostasis is controlled by a complex coagulation cascade. The cascade consists of numerous coagulation factors (>29): Most of them are protease. The ultimate step (clot formation) is the conversion of fibrinogen to fibrin by thrombin. Coagulation disorders accelerate or delay the generation of thrombin. The disclosed chip is designed to mix blood plasma with fluorogenic substrate at certain time steps to determine the amount of thrombin generated after each time step. This will generate a thrombogram that might allow the determination of the peak time for thrombin generation. The peak time is used to determine any blood coagulation disorder such as hemophilia.

The chip may include a plurality of chip sections each including three reservoirs; one of the three reservoirs containing blood plasma, another of the three reservoirs containing fluorogenic substrate, and the other of the three reservoirs being a timer reservoir. The chip sections are disposed serially along a main channel are operated one after the other. In other words, these three reservoirs are repeated several times to have multiple reading at different time steps. The design of the first two reservoirs might allow for equal mixing of the blood plasma and the fluorogenic substrate, and the third reservoir is a timer reservoir that contains sacrificial liquid for adjusting the time steps.

In one aspect, there is provided a capillary microfluidic circuit comprising reservoirs; a main channel extending between an inlet and a flow inducing element, the main channel defining inlets distributed along the main channel and each fluidly connectable to a respective one of downstream ends of the reservoirs, upstream ends of the reservoirs fluidly connectable to vents for filling the reservoirs; a conduit disposed between a first reservoir and a second reservoir of the reservoirs, a downstream end of the first reservoir linked to an upstream end of the second reservoir via the conduit.

BRIEF DESCRIPTION OF THE DRAWINGS

Reference is now made to the accompanying figures in which:

FIG. 1b is a schematic layout showing assembled domino microfluidic chip following the symbolic layout of FIG. 1a;

FIGS. 5b are schematic optical micrographs illustrating patterned (1) and unpatterned (2) control region of the domino chip of FIG. 5a;

FIGS. 5c to 5j are schematic views illustrating a draining sequence of the domino chip of FIG. 5a;

FIG. 6b is a schematic enlarged view of a portion of the domino chip of FIG. 6a;

FIGS. 6c to 6h are schematic views illustrating a draining sequence of the domino chip of FIG. 6a.

FIG. 9b is a schematic top elevation view of a portion of the domino chip of FIG. 9a.

DETAILED DESCRIPTION

Figure 1A:
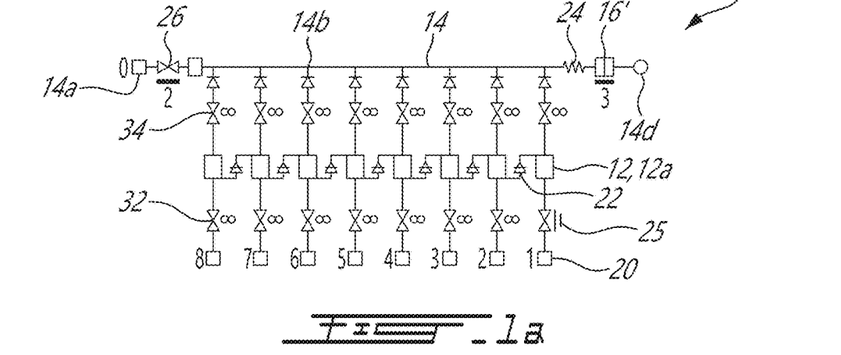
FIG. 1a is schematic symbolic layout showing capillaric microfluidic elements in accordance with one embodiment.
Figure 1B:
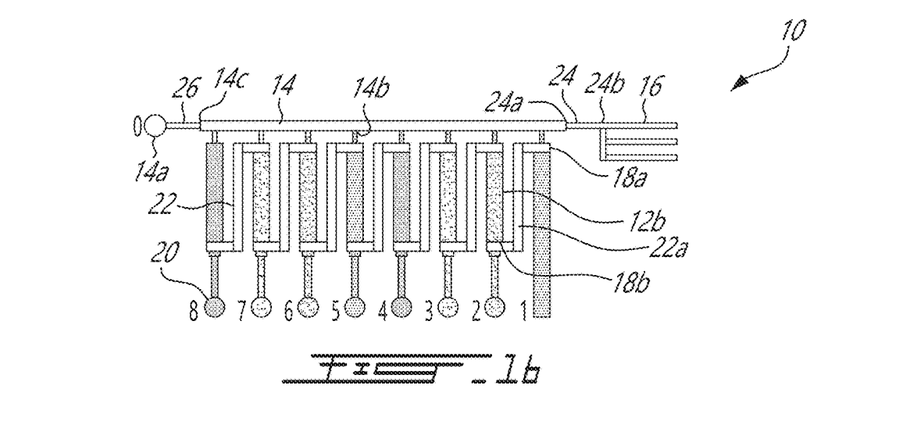
Figure 1C:
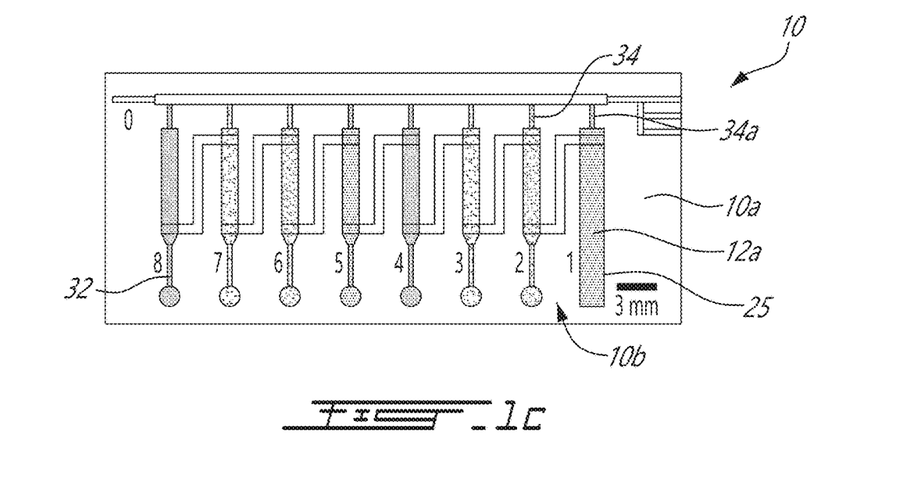
FIG. 1c is a schematic top elevation view of the assembled domino microfluidic chip of FIG. 1b.

Referring to FIGS. 1a to 1c, a capillary microfluidic chip 10, referred to herein as a domino capillary chip (DCC), or simply chip, is shown. The chip 10 may be used to successively deliver a plurality of fluids at different time intervals. The chip 10 includes reservoirs 12 for containing liquids, a main channel 14 extending between an inlet 14a thereof and a flow inducing element 16', which, in the embodiment shown, is a capillary pump 16. Alternatively, the flow inducing element 16' may be a positive pressure pump. The flow inducing element 16' is able to generate a pressure differential along the main channel 14. The flow inducing element 16' may create the positive pressure by injecting air or another suitable gas into the main channel 14 to force a liquid transfer therein using the positive pressure of the air, rather than a negative pressure. The main channel 14 defines intermediary inlets 14b that are distributed there along. Each of the intermediary inlets 14b is fluidly connectable to a respective one of downstream ends 18a of the reservoirs 12. In the embodiment shown, upstream ends 18b of the reservoirs 12 are fluidly connectable to vents 20 for filling the reservoirs 12 with the liquids. The filling of the reservoirs 12 may be carried via capillary action.

The reservoirs 12 may contain each a liquid being different than liquids contained in a remainder of the reservoirs 12. A liquid contained in the main channel 14 may be different than all of the liquids contained in the reservoirs 12. More than one reservoirs 12 may contain a same liquid. The main channel 14 may contain a liquid corresponding to that contained in one or more of the reservoirs 12.

As described in more detail below, the intermediary inlets 14b of the main channel 14 simultaneously act as trigger valves stopping the flow of the reservoir as it is filled, and allowing it to flow in the main channels after the main channels are filled. The inlets 14b also act as retention valves upon drainage of the reservoirs 12, preventing air from filling into the main channel 14. The vents 20 also act as retention valves, preventing drainage of the reservoirs 12 by the sole action of the capillary pump 16. Additional details regarding the valving are provided herein below.

In the embodiment shown, the chip 10 has eight side branches, or reservoirs 12. It is understood that more or less reservoirs 12 may be used without departing from the scope of the present disclosure. The disclosed chip 10 is configured for delivering nine liquids. Eight liquids from the reservoirs 12 whose draining is triggered by adding a solution, or ninth liquid, to the main channel 14 via its inlet 14a.

In the embodiment shown, the chip 10 further comprises a flow resistor 24 having an inlet 24a fluidly connected to the main channel 14 and an outlet 24b fluidly connected to the flow inducing element 16'. The flow resistor 24 may be used to control a flow rate of the liquid(s) toward the flow inducing element 16'.

The chip 10 further includes a first retention burst valve 25 at an upstream end of a first one 12a of the reservoirs 12 and a second retention burst valve 26 fluidly connected to an upstream end 14c of the main channel 14 upstream of the intermediary inlets 14b of the main channel 14. In the embodiment shown, the retention burst valve 26 is defined by a section of the main channel 14 having at least one of a height or a width less than that of a remainder of the main channel 14.

Both of the first and second retention burst valves 25, 26 are designed to have a bursting pressure less than a negative pressure generated by the capillary pump 16. In the depicted embodiment, the first retention burst valve 25 has a bursting pressure less than that of the second retention burst valve 26 such that, when subjected to the negative pressure induced by the capillary pump 16, the first retention burst valve 25 bursts, but not the second retention burst valve 26. As will be described below, the second retention burst valve 26 is configured to burst after all of the reservoirs 12 have been drained by the capillary pump 16. The first and second retention burst valves 25 and 26 are configured to burst at a respective predefined pressure encoded by the valve height and width.

The chip 10 further includes a first set of retention valves 32 and a second set of retention valves 34. The retention valves 32 of the first set are disposed downstream of the vents 20 and upstream of the upstream ends 18b of the reservoirs 12. The retention valves 34 of the second set are downstream of the ends 18a of the reservoirs 12 and upstream of the main channel 14. The valves 32 and 34 have bursting pressures being greater than the negative pressure of the capillary pump 16. Stated otherwise, the capillary pump 16 is not strong enough to draw the liquid out of the valves 32, 34 after the reservoirs 12 are emptied.

Capillary forces vary in function of a plurality of parameters, such as the surface tension of the liquid, the angles of contact between the liquid and a channel containing the liquid, and the dimensions of the channel. In the embodiment shown, the retention valves 32, 34 are constrictions between the reservoirs 12, the main channel 14, and the vents 20. The retention valves 32, 34 are used to prevent undesired drainage of the reservoirs 12. Additional details about this aspect are presented herein below.

Previously, sequential drainage of the liquids of each of the reservoirs 12 was achieved by designing valves located upstream and downstream of the reservoirs 12 each with a corresponding bursting pressure being inferior than a negative pressure generated by the capillary pump 16. Therefore, once the chip 10 is activated, the valve having the lowest bursting pressure would burst first and the liquid contained in an associated one of the reservoirs 12 would be emptied toward the capillary pump 16 via the main channel 14. Then, the valve having the second lowest bursting pressure would burst to allow the liquid contained in its associated reservoir 12 to empty toward the pump 16. This process would go on until all of the reservoirs 12 are emptied. As the person skilled in the art may appreciate, it would be difficult to add reservoirs because of limitations in manufacturing techniques. In other words, there is a practical limitation to the number of valve that can be manufactured to obtain a great number of different bursting pressures.

All the valves of the first set of valves 32 may be identical and all the valves of the second set of valves 34 may be identical. In the depicted embodiment, the valves 32, 34 are the constrictions having dimensions less than that of the reservoirs 12 and a bursting, or capillary, pressure that exceeds that of the capillary pump 16 to prevent the liquids from being drained out of the retention 32, 34 valves by the capillary pump 16. Accordingly, the retention valves 32, 34 have a pressure exceeding that of the capillary pump 16. If a valve is smaller than the reservoir 12, but has a bursting pressure less than the negative pressure induced by capillary pump 16, then it is a retention burst valve. Hence, the retention valves 32, 34 of the first and second sets provide a valving function by having at least one of a height or a width of the channels less than that of the reservoirs 12 and by generating an equal or greater negative pressure than that of the capillary pump 16.

To provide sequential drainage of the reservoirs 12, air conduits 22 are disposed between each adjacent two of the reservoirs 12. More specifically, a first conduit 22a is disposed between a first one of the reservoirs 12a and a second one of the reservoirs 12b via the first air conduit 22a. The downstream end 18a of the first reservoir 12a is linked to the second reservoir 12b. In the depicted embodiment, the air conduit is linked to the upstream end 18b of the second reservoir 12b via the first air conduit 22a. Stated otherwise, each one of the first seven reservoirs 12 is connected to a subsequent one of the eight reservoirs 12 via an air conduit 22. Each of the reservoirs 12 is serially, or sequentially, connected to ambient air via the air conduits 22. The downstream ends 18a of the reservoir 12 are each connected to a respective one of the inlets or vents 20 for filling the reservoirs 12. The first reservoir 12a is downstream of the second reservoir 12b relative to a flow of liquid circulating in the main channel 14 toward the capillary pump 16.

Herein, "subsequent" does not necessarily mean "adjacent". In other words, one of the air conduits 22 may connect two reservoirs that are separated by one or more of the other reservoirs 12. It is understood that the first reservoir to be drained by the capillary pump 16 is not necessarily the one closest to said pump 16.

The air conduits 20 allow to bypass the retention valves 32 whose bursting pressures are greater than the negative pressure of the pump 16. By connecting one of the reservoirs 12 to air via one of the air conduits 20, the liquid contained in said reservoir may be drained because the one of the air conduits allows air to replace the content of the one of the reservoirs 12. Stated differently, the air conduits 20 may permit the force generated by the retention valves 32 to be "cancelled", thereby permitting the liquid of the reservoirs 12 to be drained without influence by the retention valves 32.

To start the process, a liquid, which in one particular embodiment may be water, is injected in the inlet 14a of the main channel 14. The liquid moves via capillary force in the main channel 14 until it reaches the capillary pump 16 that exert a suction pressure on the liquid. When the pressure reaches a given threshold, the first retention burst valve 25 of the first reservoir 12a bursts and the first reservoir 12a starts draining its content toward the capillary pump 16.

Once the first reservoir 12a is drained and the air flowing in reaches the end 18a, it can fill the conduit 22a, and the upstream end 18b of the second reservoir 12b becomes fluidly connected to air thereby bypassing its associated retention valve 32. The air connection now allows draining of the reservoir 12b while the drained liquid is replaced by air sucked in via the reservoir 12a and the air conduit 22a. After reservoir 12b is drained, air fills the next reservoir. This process goes on, reservoir by reservoir, until all the liquids of the reservoirs 12 are drained by the capillary pump 16.

After all of the reservoirs 12 have been drained, the second retention burst valve 26 bursts, and the main channel 14 is also drained into the capillary pump 16. Alternatively, the second retention burst valve 26 may be replaced by a retention valve having a bursting pressure greater than the capillary pump pressure such that the main channel 14 is prevented from being drained by the pump 16. As shown in FIG. 1a, the capillary pump 16 has the greatest negative pressure within level 3, while the RBV 26 is in level 2, and the RBV 25 is in level 1, and thus is the first to burst.

When all of the reservoirs 12 are filled with liquids, drainage of the reservoirs is prevented by the retention valves 32, which, as aforementioned, have each a bursting pressure greater than the pressure generated by the capillary pump 16. Before the drainage begins, the pressure in all reservoirs 12 and conduits 22 is substantially equal. The drainage thus starts when the first retention burst valve 25 bursts upstream of reservoir 12a. As air presents a much lower flow resistance than liquid, it can readily fill all the reservoirs in series as they are being drained without adding significant resistance to the flow in the circuit.

The main channel 14 triggers liquid release from the side branches to which the reservoirs 12 are connected. The first retention burst valve 25 is used to trigger the serial drainage of the other conduits that are protected by the retention burst valves 32. The first branch is the first to drain its content in the circuit.

Referring now more particularly to FIG. 1c, the chip 10 includes two layers: a hydrophilic hydraulic layer 10a and a hydrophobic pneumatic layer 10b. The hydrophilic hydraulic layer 10a includes the reservoirs 12, the vents 20, and the capillary pump 16. The symbolic and schematic illustrations of these microfluidic elements are shown in Figs. 1a and 1b, respectively. The hydrophobic pneumatic layer 10b includes the air conduits 22, also referred to as microchannels. The hydraulic layer 10a is sealed with the pneumatic layer 10b. As illustrated, the air conduits 22 are defined by the pneumatic layer 10b. The reservoirs 12, the vents 20, and the capillary pump 16 are defined by the hydrophilic hydraulic layer 10a.

In the embodiment shown, the vents 20 remain uncovered by the pneumatic layer 10b because they are used to fill the reservoirs 12. A liquid is injected in the vents 20 and is automatically pumped in a respective one of the reservoirs 12 via capillary force.

Figure 2:
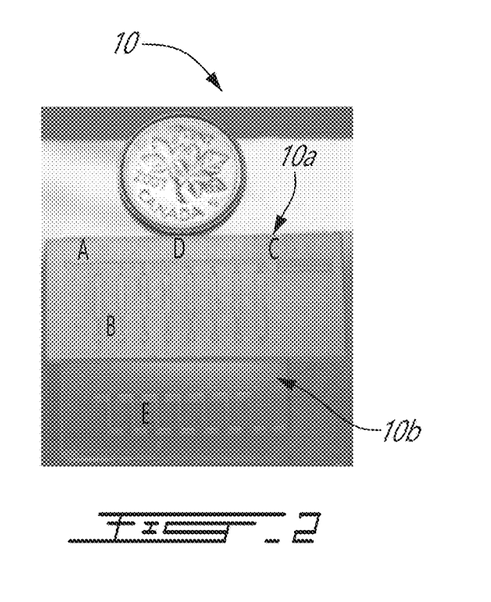
FIG. 2 is a schematic view of a 3D-printed hydraulic and pneumatic layers of the domino chip of FIG. 1b.

Referring now to FIG. 2, a 3D-printed hydraulic layer 10a and polydimethylsiloxane (PDMS) pneumatic layer 10b of the domino chip 10 are shown unassembled. As shown, the pneumatic layer 10b defines the air conduits 22 whereas the 3D-printed hydraulic layer 10a defines a remainder of the elements. More specifically, the air conduits 22 are defined within a thickness of the pneumatic layer 10b. The pneumatic layer 10b defines two opposed faces. A depth of the air conduits 22 extends from one of the two opposed faces toward the other of the faces. In the embodiment shown, the chip 10 includes seven air 22 conduits and two retention burst valve types different from one another by their size.

In the embodiment shown, the hydraulic layer 10a is 3D-printed using transparent resin in a Miicraft 100 printer in 10 minutes and is plasma-treated for 60 seconds at 150 Watts for hydrophilicity. The pneumatic layer 10b is made from 1:20 polydimethylsiloxane (PDMS) replicated from a 3D-printed mold and sealed to the hydraulic layer. Pneumatic layers 10b are hydrophobic thus forming air conduits 22 by preventing filling by liquids. Cleanroom paper was used as a high volume, small footprint capillary pump 16. Other suitable capillary pump may be used. The air conduits 22 may be etched in the pneumatic layer 10b.

Figure 2A:
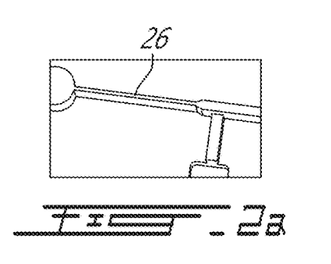
FIGS. 2a to 2e are schematic enlarged views of different areas of the 3D-printed hydraulic chip of FIG. 2.
Figure 2B:
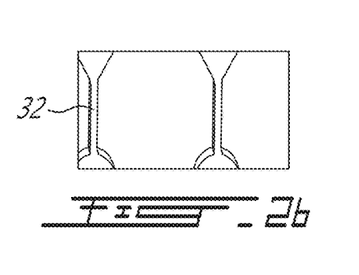
Figure 2C:
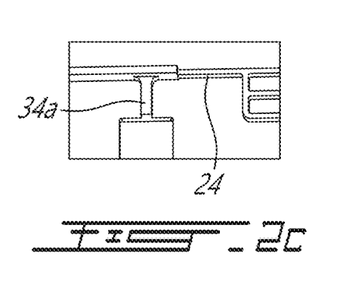
Figure 2D:
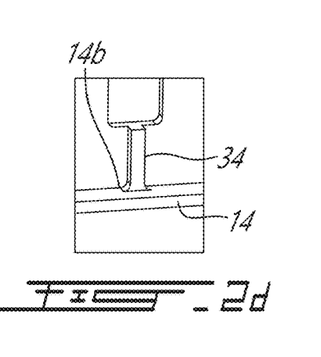
Figure 2E:
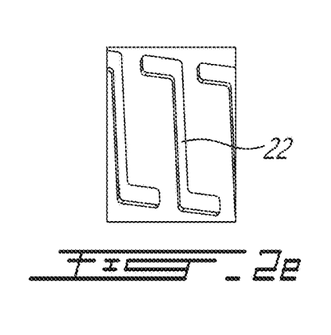

The inlets or vents 20 are shown in FIG. 2a, the upstream ends 18a of the reservoirs 12 are shown in FIG. 2b, the flow resistor 24 and the capillary pump 16 are shown in FIG. 2c, one of the trigger valves 34 is shown in FIG. 2d, the air conduits 22 are shown in FIG. 2e.

In the embodiment shown, a size of the microchannels on the hydraulic layer 10a ranges from 50×150 µm$^2$ for the trigger valve 32, 34 to 500×1000 µm$^2$ for the reservoirs 12. The air conduits 22 on the pneumatic layer 10b are 300× 1000 µm$^2$. The white scale bars on the FIGS. 2a to 2e have a length of 1 mm.

Figure 3A:
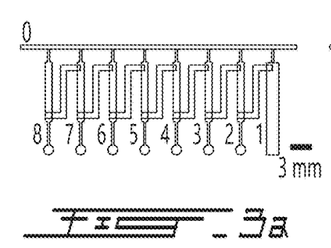
FIGS. 3a to 3l are schematic views illustrating a sequential drainage of eight reservoirs of the chip of FIG. 1b by domino microfluidics.
Figure 3B:
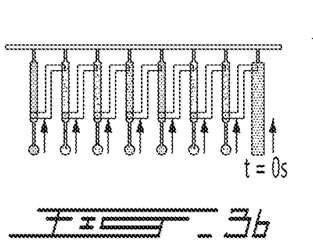
Figure 3C:
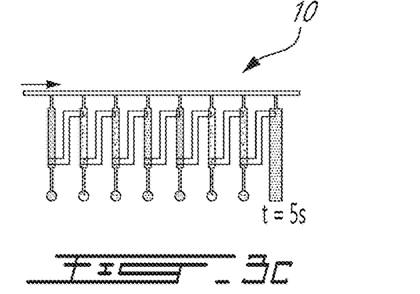
Figure 3D:
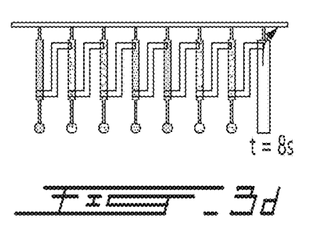
Figure 3E:
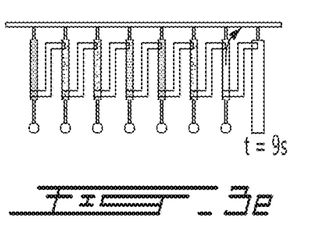
Figure 3F:
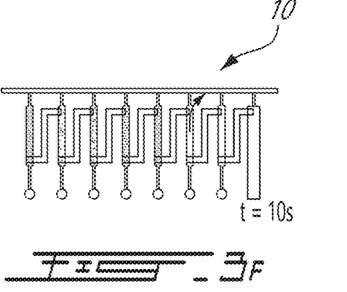
Figure 3G:
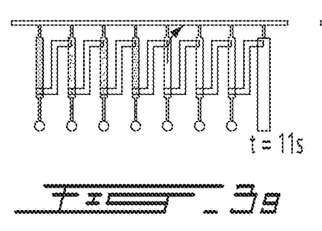
Figure 3H:
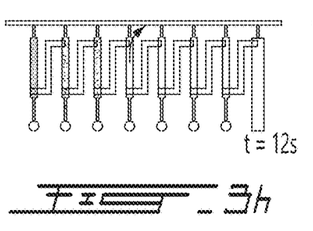
Figure 3I:
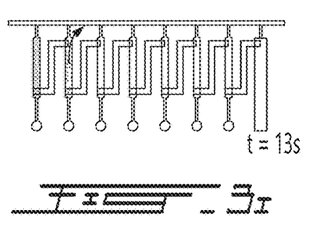
Figure 3J:
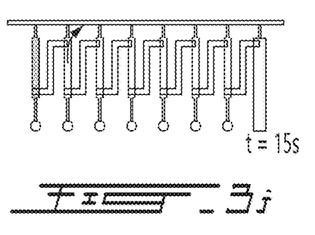
Figure 3K:
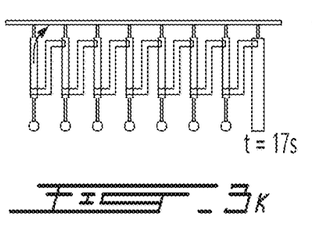
Figure 3L:
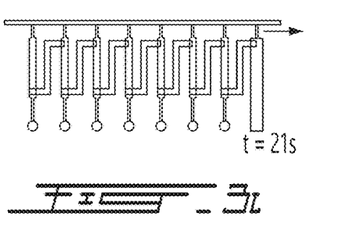

Referring now to FIGS. 3a to 3l, a sequential drainage of the eight reservoirs 12 of the chip 10 of FIG. 1a by domino microfluidics is shown. More specifically, FIGS. 3a to 3l display time-lapse images showing the sequential drainage of the reservoirs 12 using repeats of an identical air conduit 22. The chip 10 is triggered by loading the main channel 14 at t=5s (FIG. 3c) via its inlet 14a. Once the valve 34a upstream of the first reservoir 12a bursts, a first one of the air conduits 22 connecting the downstream end 18a of the first reservoir 12b to the upstream end 18a of the second reservoir 12b opens allowing drainage of the second reservoir 12b (t=9 s) (FIG. 3e). Subsequently, a second one of the air conduits 22 opens leading to drainage of a next one of the reservoirs 12 (t=10 s) (FIG. 3O, and so on until all reservoirs 12 are emptied.

Figure 4A:
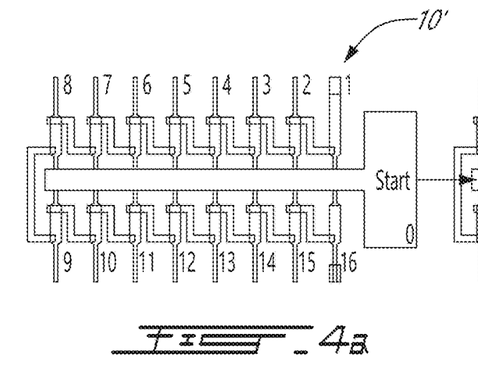
FIGS. 4a and 4b are schematic views of a sequential drainage of sixteen reservoirs by domino microfluidics of a domino microfluidic chip in accordance with another embodiment.
Figure 4B:
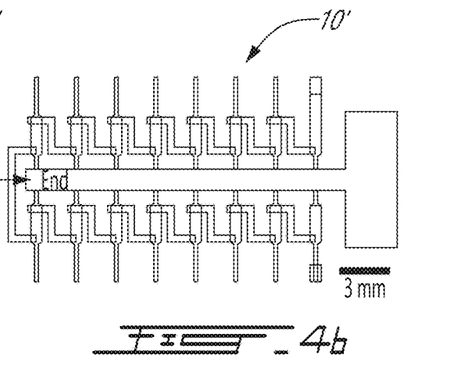

Referring now to FIGS. 4a and 4b, another embodiment of a chip 10' containing sixteen reservoirs 12 and fifteen air conduits 22 is shown. A sequential drainage of the sixteen reservoirs 12 by domino microfluidics is illustrated from the start (FIG. 4a) to the end (FIG. 4b). In the embodiment shown, the sequential drainage of all of the sixteen reservoirs 12 was accomplished in less than one minute using identical air conduits 22 as for the embodiment of FIG. 1. A length of the air conduit between the eighth and the ninth reservoir is longer than a length of the air conduits between other reservoirs to fit the serpentine shape of the device. The chip 10' of FIG. 4 is designed for sequential drainage of seventeen liquids.

Figure 5A:
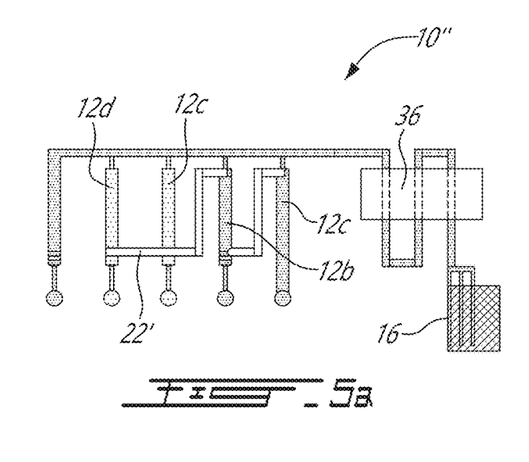
FIG. 5a is a schematic view of a domino chip in accordance with another embodiment.

Referring now to FIG. 5a, a domino microfluidic chip 10''' that may be used for silver enhancement in accordance with another embodiment is shown. The chip 10''' is configured for the simultaneous delivery of two solutions by extending an air conduit 22' over two reservoirs 12c, 12d that may be respectively filled with a silver salt and a reducing agent. In the embodiment, the two reservoirs 12c, 12d may be simultaneously emptied using the common air conduit 22'. Stated otherwise, the air conduit 22' further links an upstream end 18b of a fourth reservoir 12d to the downstream end 18a of the second reservoir 12b via the upstream end 18b of the third reservoir 12c. In the embodiment shown, the fourth reservoir 12d is upstream of the third reservoir 12c.

In the embodiment shown, the two solutions that are drained simultaneously are a silver salt and reducing agent. These liquids are unstable when mixed prior to the reaction. Similarly to the sequential drainage illustrated in FIG. 1a, simultaneous drainage might be scaled up by extending the air conduit 22' over three or more channels, or reservoirs 12.

Figure 5B:
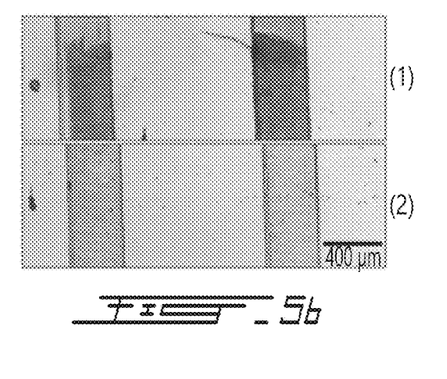
Figure 5C:
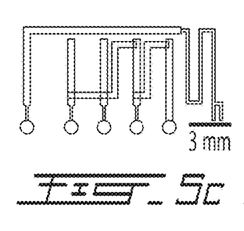
Figure 5D:
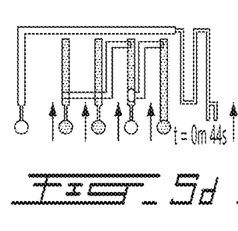
Figure 5E:
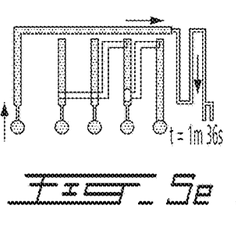
Figure 5F:
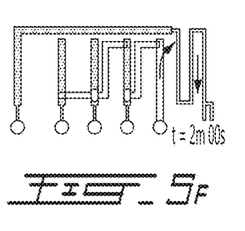
Figure 5G:
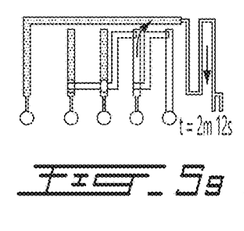
Figure 5H:
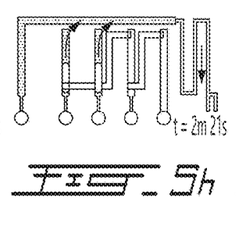
Figure 5I:
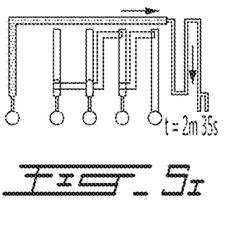

The chip 10''' further includes a reaction zone 36 fluidly connected to the main channel 14 and upstream of the capillary pump 16. As shown in FIG. 5b, the reaction zone 36 may be patterned with Streptavidin-Nanogold. In this regard, FIG. 5b shows optical micrographs showing differential colorimetric signal between reaction zone 36 patterned with streptavidin-nanogold (1) and unpatterned (2).

Figure 5J:
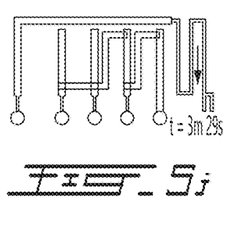

FIGS. 5c to 5j show time-lapse images with aqueous food dye. As shown, at t=44 s (FIG. 5d), all of the reservoirs are full. At t=1 m 36 s (FIG. 5e), the retention burst valve bursts thereby starting the draining. First, the water from the main branch 14 flows toward the reaction zone 36. At t=2 m (FIG. 5f), water from the first reservoirs 12a starts to drain toward the reaction zone 36. At t=2 m 12 s (FIG. 5g), water from the second reservoir 12b starts to drain toward the reaction zone 36. At t=2 m 21 s (FIG. 5h), reducing agent contained in the third reservoir 12c and the silver salt contained in the fourth reservoir 12d simultaneously start to drain in the reaction zone 36. At t=2 m 35 s (FIG. 5i), water from the main channel 14 is totally drained therefrom toward the reaction zone 36. The process is finished at t=3 m 29 s (FIG. 5j).

Figure 6A:
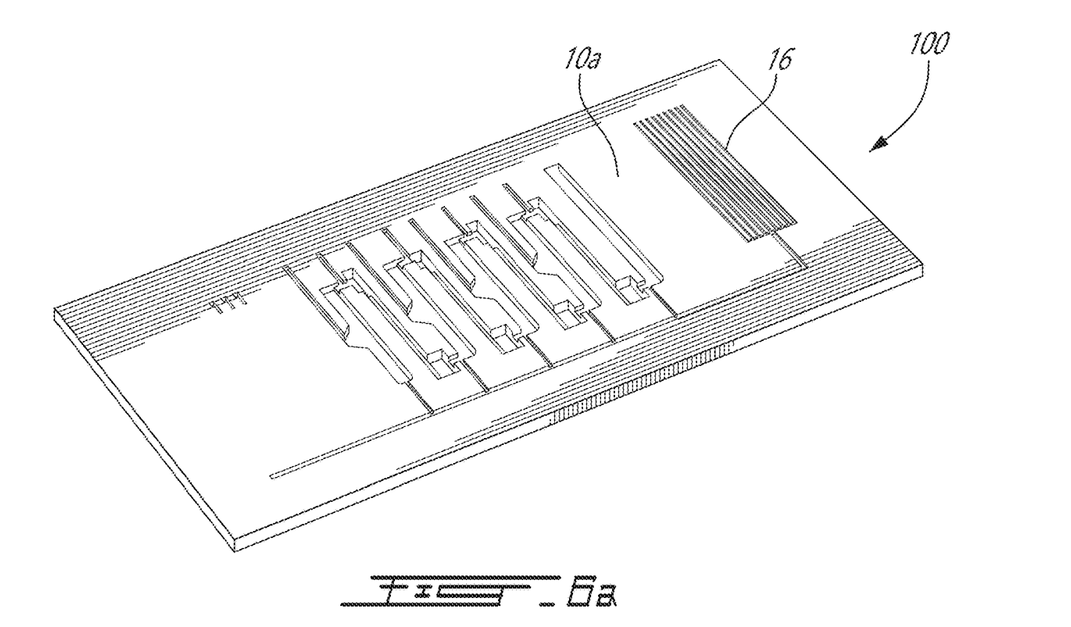
FIG. 6a is a schematic tridimensional view of a domino chip in accordance with another embodiment.
Figure 6B:
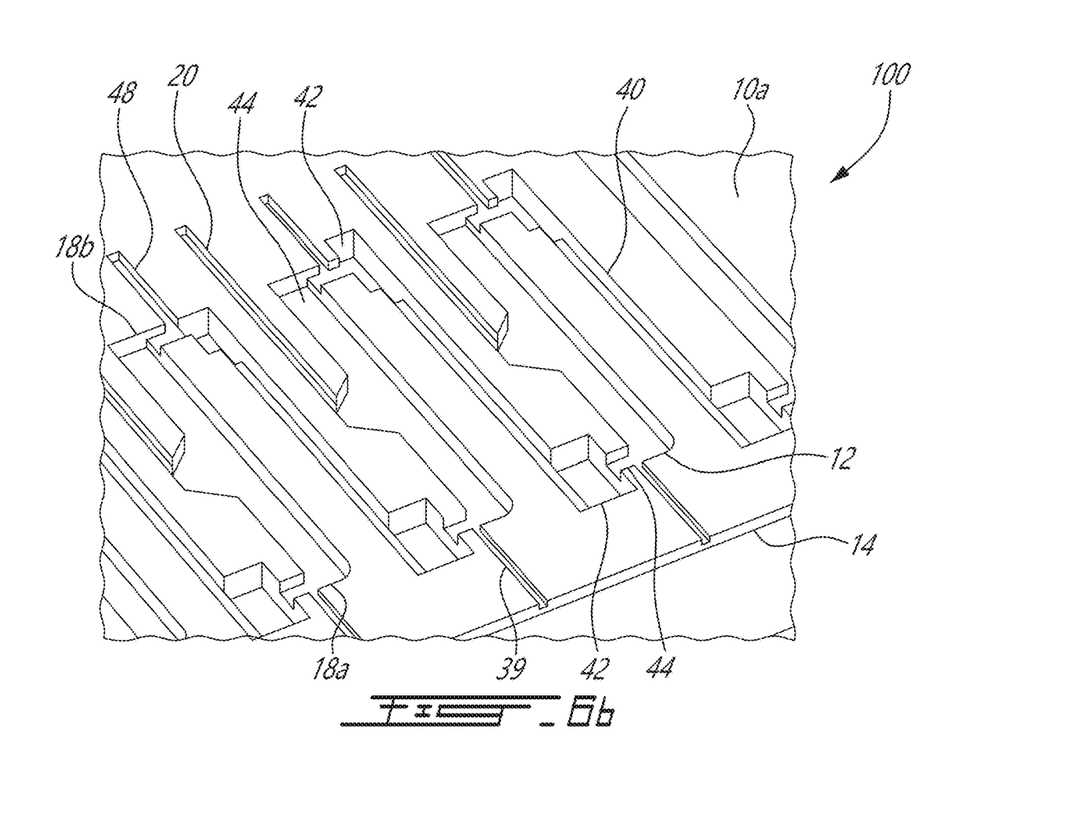
Figure 6C:
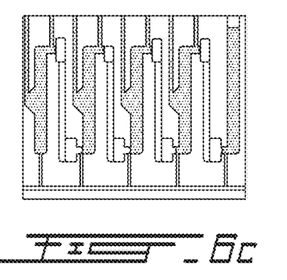
Figure 6D:
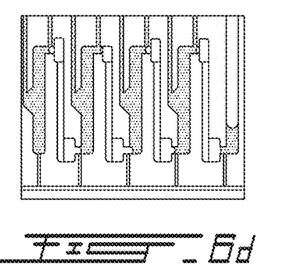
Figure 6E:
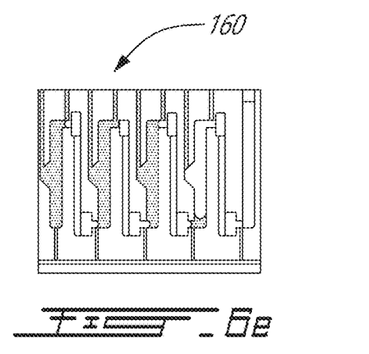
Figure 6F:
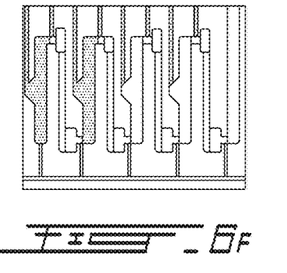
Figure 6G:
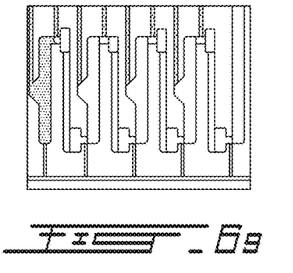
Figure 6H:
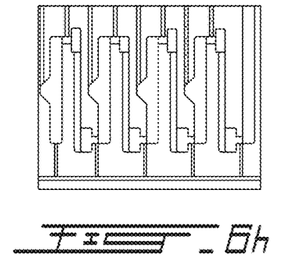

Referring now to FIGS. 6a and 6b, a domino microfluidic chip 100 in accordance with another embodiment is shown. Each of the reservoirs 12 is operatively connected to a trigger valve 39, which may be similar to the valve 32, 34 described herein below, at its downstream end 18a. In the embodiment shown, the air conduits are replaced by channels 40 defined through the hydraulic hydrophilic layer 10a and each placed between two reservoirs 12. Each of the channels 40 extends between opposite ends that each define air traps 42. The ends 18a, 18b of the reservoirs 12 are fluidly separated from the channels 40 via stop valves 44.

The chip 100 further includes air vents 48 extending from the upstream ends 18b of the reservoirs 12. The air vents 48 might allow the filling of the reservoir 12 in a non-sequential manner. FIGS. 6c to 6h illustrates the drainage of the chip 100 of FIG. 6a, which proceeds in a similar manner than the draining of the chip 10 described with reference to FIG. 1a.

This single-layer structure of the chip 100 might allow the DCC to be sealed by using a flat piece of PDMS or tape. Single-layer DCCs might be faster to fabricate since they might be directly 3D-printed in less than ten minutes and sealed with a piece of tape, PDMS, or other adhesive material.

In a particular embodiment, one could change the cover of the chip so that instead of enabling sequential drainage, one obtains simultaneous drainage of reservoirs, but extending one air conduit over two liquid reservoirs. The cover may include multiple layers of covers that are stacked on top of each other, with access holes between them. That might allow an air conduit to connect two reservoirs that are not adjacent to one another via the access hols.

In a particular embodiment, DCCs are designed so that the sizes and volumes of different reservoirs are different. Air conduits can connect identical reservoir sizes, smaller reservoirs to bigger reservoirs, or vice-versa.

The drainage time of individual reservoirs might be controlled independently by placing flow resistors along the flow path of each reservoir. This might allow unique timing of each liquid delivery step independently of the others.

Figure 7:
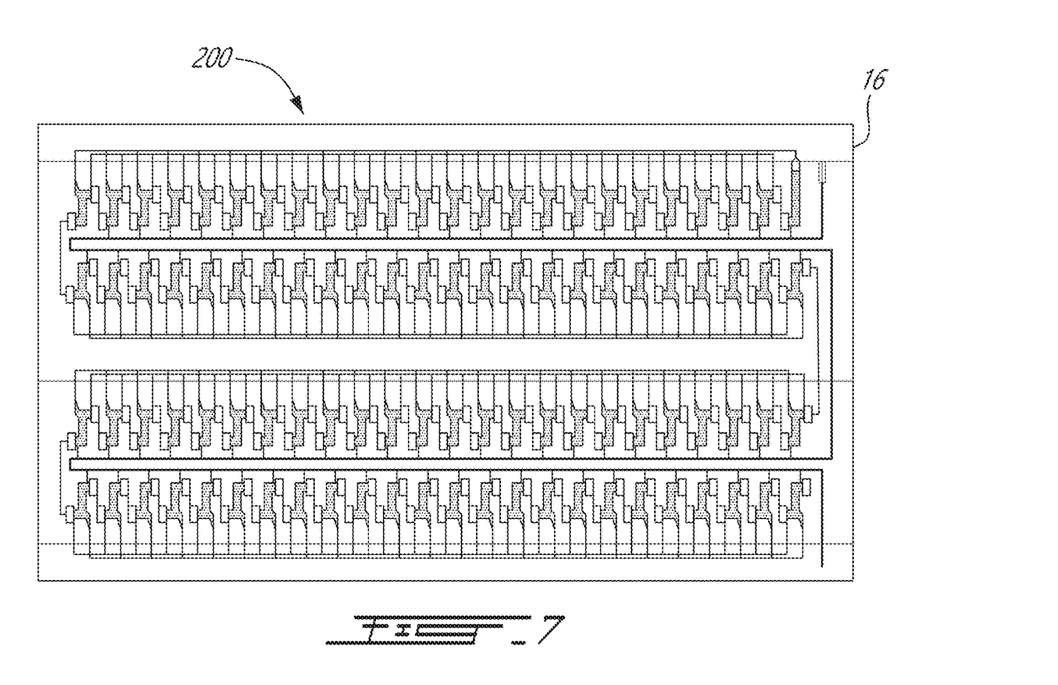
FIG. 7 is a schematic top elevation view of a domino chip in accordance with another embodiment.

FIG. 7 shows another embodiment of a chip 200 having 96 reservoirs 12. The reservoirs 12, valves 39, channels 40, air pockets 42, stop valve 44, air vents 48 are identical to the chip 100 of FIG. 6a. FIG. 7 illustrates the scalability potential of the disclosed concept.

Figure 8:
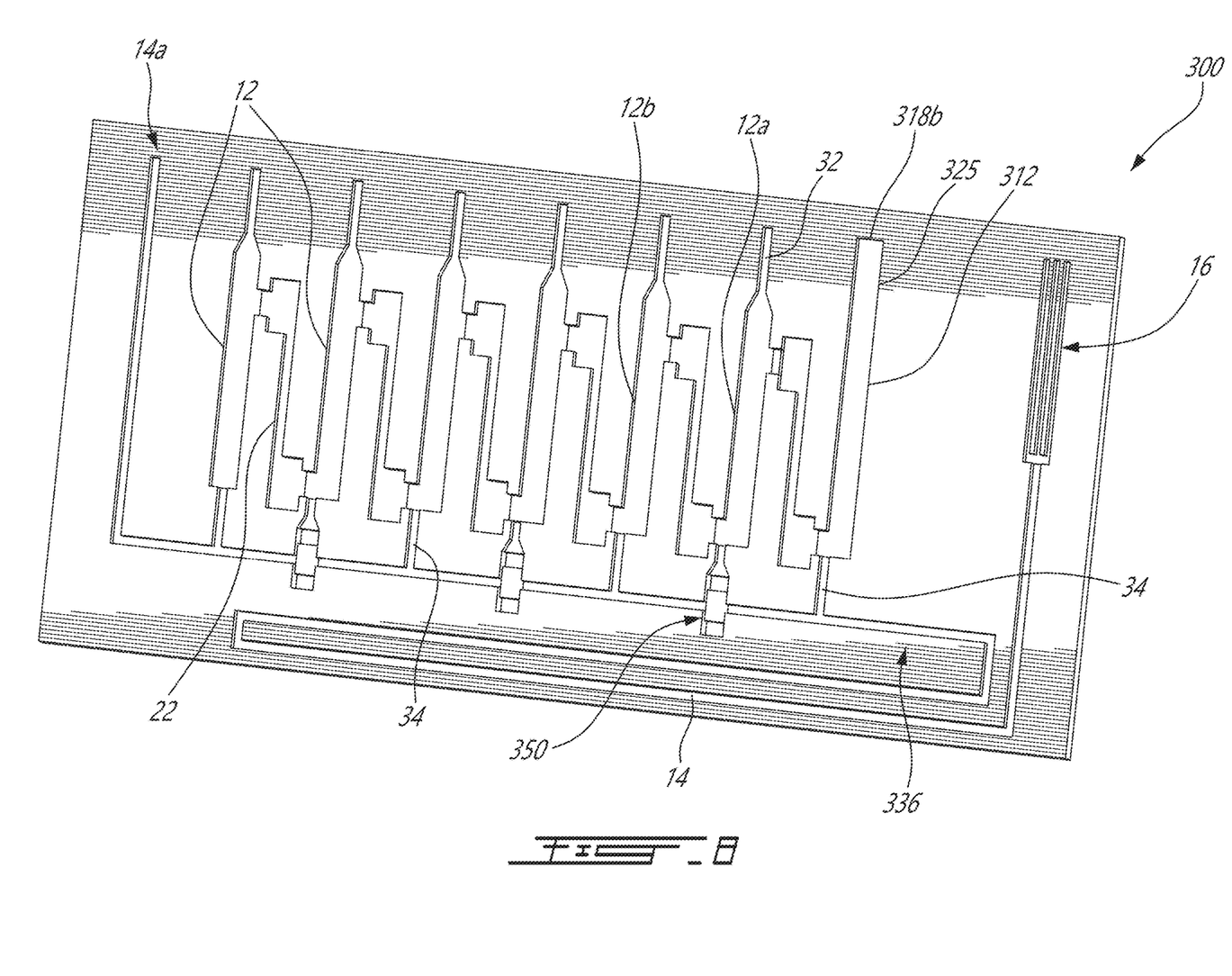
FIG. 8 is a schematic top elevation view of a domino chip in accordance with another embodiment.

Referring now to FIG. 8, another embodiment of a chip is generally shown at 300. The chip 300 includes substantially the same elements of the previously described chips, namely, the reservoirs 12, the air conduits 22, the capillary pump 16, the valves 32, 34, and the main conduit 14. The main channel 14 further defines a reaction chamber 336 upstream of the capillary pump 16.

An issue with the above describes chips is that, once it is started, it cannot be stopped until all of the reservoirs 12 are emptied. However, for some applications, it might be advantageous temporarily halt the drainage of the reservoirs 12 for allowing time for the liquids drained from some of the reservoirs 12 to react in the reaction chamber 336.

In the depicted embodiment, the chip 300 has a sacrificial reservoir 312 configured for stopping the drainage of the liquids from the reservoirs 12 by the capillary pump 16. The drainage of the reservoirs 12 resumes after the sacrificial reservoir 312 is emptied. The time by which the drainage is stopped may be tuned by designing the sacrificial reservoir 312 to contain a given volume of sacrificial liquid and with knowledge of the geometry of the components of the chip 300 that will dictate a drainage flow rate of the sacrificial reservoir 312. In other words, the sacrificial reservoir 312 acts as a programmable timer that stops and restores the reservoir drainage. In the embodiment shown, the sacrificial reservoir 312 is upstream of the reaction chamber 336.

The process is started by injecting a liquid in the main channel 14 via its inlet 14a. Then, a retention burst valve 325 located at an upstream end 318b of the sacrificial reservoir 312 bursts and its content is drained in the main channel 14 and in the reaction chamber 336. During the drainage of the sacrificial reservoir 312, the other reservoirs 12 remain filled. After the drainage of the sacrificial reservoir 312, the air conduit 22 connects a downstream end of the sacrificial reservoir 312 to an upstream end of a first one 12a of the reservoirs 12, which thereby starts to drain in the main channel 14. The sacrificial liquid in the sacrificial reservoir 312 is incubated in the reaction chamber 336 until the sacrificial reservoir 312 is completely drained.

At which point, the liquid contained in the first one 12a of the reservoirs 12 starts to drain in the main channel 14. In the embodiment shown, the first one 12a of the reservoirs 12 is connected to the main channel 14 via a bridge 350 that allows the liquid of the first one of the reservoirs 12 to flow toward the capillary pump 16 by bypassing the reaction chamber 336.

After the first one 12a of the reservoirs 12 is emptied, a second one 12b of the reservoirs 12 starts to drain in the main channel 14. As shown, the liquid contained in the second one 12b of the reservoirs 12 will circulate in the reaction chamber. Such incubation step may be occur repeatedly as the reservoirs 12 are drained toward the capillary pump 16. It is understood that any combination of the above disclosed reservoirs 12, bridges 350, sacrificial reservoir 312, and reaction chamber 336 may be used to achieve a variety of different drainage pattern. More than one reaction chamber 336 and/or more than one sacrificial reservoir 312 may be used without departing from the scope of the present disclosure.

Figure 9A:
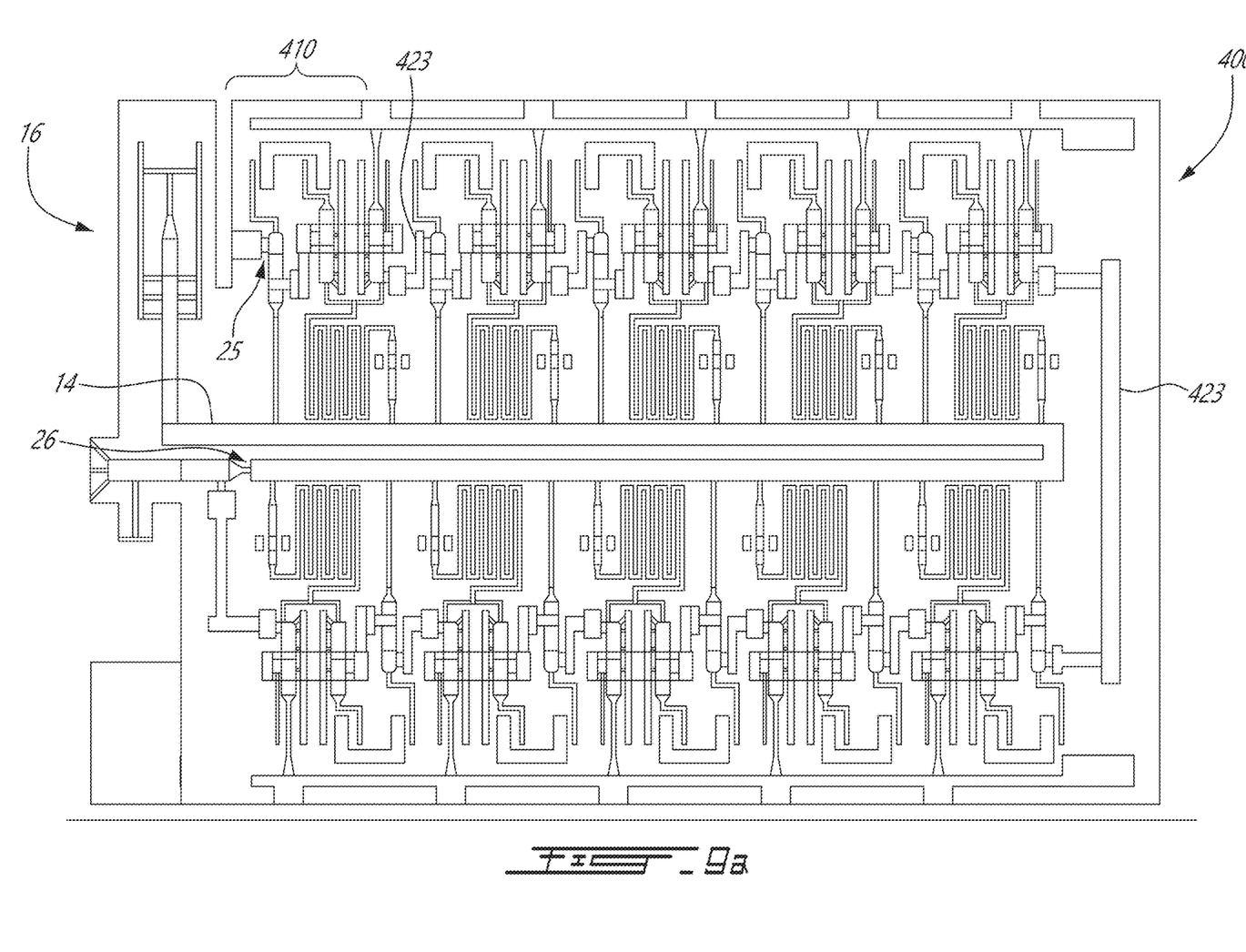
FIG. 9a is a schematic top elevation view of a domino chip in accordance with another embodiment.
Figure 9B:
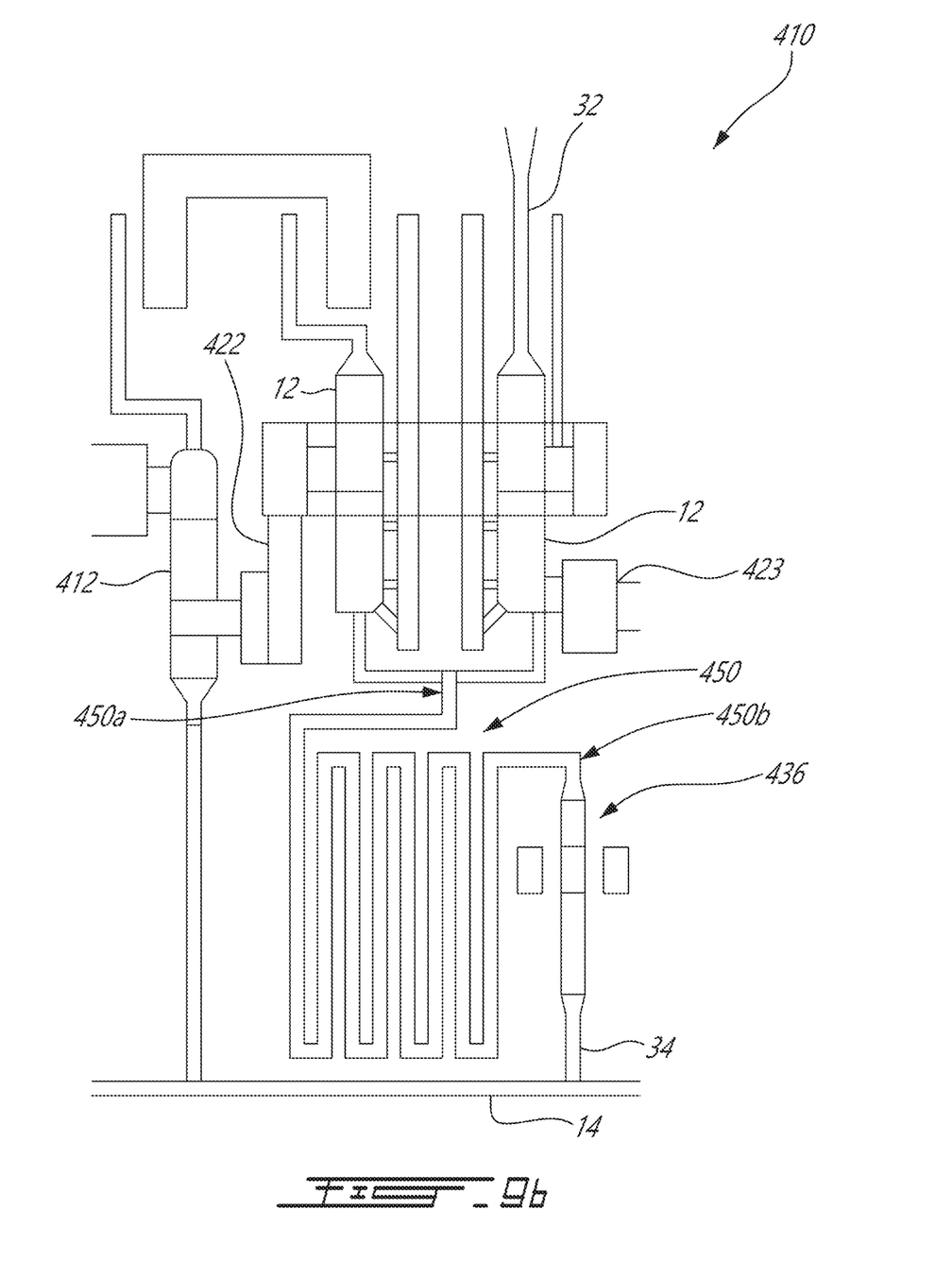

Referring now to FIGS. 9a and 9b, a chip in accordance with another embodiment is generally shown at 400. The chip 400 includes a plurality of cells 410, ten in the embodiment shown, each disposed along a main channel 14. Each of the cells 410 includes three reservoirs namely, a sacrificial reservoir 412 and two regular reservoirs 12, and an air conduit 422 that connects the sacrificial reservoir 412 to both of the two regular reservoirs 12. Each of the cells 410 includes a serpentine mixing channel 450 and a reaction chamber 436. The serpentine mixing channel 450 has an inlet 450a, which is connected to both of the regular reservoirs 12, and an outlet 450b, which is connected to the main channel 14 via the reaction chamber 436. The chip 400 further includes a connecting air conduit 423 that connects one of the two reservoirs 12 to the sacrificial reservoir 412 of a subsequent cells 410. It is understood that more or less than ten cells 410 may be used without departing from the scope of the present disclosure.

The chip 400 further includes a first set of retention valves 32 disposed upstream of upstream ends of the reservoirs 12. The retention valves 32 of the first set have a bursting pressure greater than the suction pressure of the flow inducing element 16.

The chip 400 further includes a second set of retention valves 34 disposed downstream of downstream ends of the reservoirs 12 and upstream of the main channel 14. In the embodiment shown, the retention valves 34 of the second set are located downstream of the reaction chambers 436 and upstream of the serpentine mixing channel 450.

In the embodiment shown, the chip 400 may be used to analyze blood coagulation process to determine the peak time for thrombin generation. The peak time may be used to diagnose coagulation disorders. In the depicted embodiment, one of the regular reservoirs 12 contains blood plasma and the other contains fluorogenic substrate. The sacrificial reservoir 412 contains a sacrificial liquid and is used as a timer. By having a plurality of the cells 410 along the main channel, the disclosed chip 400 might allow the acquisition of multiple reading of the amount of thrombin generated at a plurality of time intervals.

In the depicted embodiment, drainage of the three reservoirs 412, 12 is initiated by air valves where the liquid contained in the sacrificial reservoir 412 drains first in the main channel 14 followed by the drainage of the blood plasma and the fluorogenic substrate each contained in a respectively one of the reservoirs 12. The drainage of the two reservoirs 12, and thus of the blood plasma and the fluorogenic substrate, occurs simultaneously after the timer (sacrificial reservoir 412) is emptied.

As previously explained with reference to FIGS. 1a to 1c, the capillary pump 16 causes bursting of the retention burst valve 25 located at an end of the sacrificial reservoir 412. Once the sacrificial reservoir 412 of a first one of the units 410 is empty, the air conduit 422 connects the two reservoirs 12, which contains the blood plasma and the fluorogenic substrate, to ambient air to start their drainage in the main channel 14 via the serpentine 450 and the reaction chamber 436. The blood plasma and the fluorogenic substrate mix within the serpentine 450 and a mix of the blood plasma and the fluorogenic substrate is stored in the reaction chamber 436. Once the two reservoirs 12 are emptied, the sacrificial reservoir 412 of a subsequent one of the cells 410 becomes connected to ambient air via the connecting air conduit 423 and drainage of said sacrificial reservoir 412 may start.

Having all the reservoirs 12 of the cells 410 are drained sequentially at different time steps might allow measuring the thrombin generation and analyze it the at the reaction chambers 436.

Embodiments Disclosed Herein Include:

A. a capillary microfluidic circuit comprising: a main channel communicating with a flow inducing element configured for generating a pressure differential in the main channel to draw one or more liquids into the main channel, the main channel having intermediary inlets distributed along the main channel; reservoirs for containing the one or more liquids prior to being drawn into the main channel, the reservoirs including a first reservoir and at least a second reservoir, each of the reservoirs having an upstream end connectable to vents for filling the reservoirs with the one or more liquids and a downstream end, the downstream end of each of the reservoirs being connected to the intermediary inlets of the main channel; and a conduit disposed between the first reservoir and the at least a second reservoir, the conduit interconnecting the downstream end of the first reservoir with the upstream end of the at least a second reservoir.

B. A capillary microfluidic circuit, comprising: a main channel extending between an inlet and a flow inducing element for generating a pressure differential for drawing a flow in the main channel; a plurality of cells each connected to the main conduit between the inlet of the main conduit and the flow inducing element, each of the plurality of cells including: a sacrificial reservoir configured for containing a sacrificial liquid, the sacrificial reservoir connected to the main channel, two reservoirs, each of the two reservoirs configured for containing a respective one of blood plasma and a fluorogenic substrate, a mixing zone having an upstream end connected to the two reservoirs, a reaction chamber connected to a downstream end of the mixing zone and to the main channel, the mixing zone connected to the main channel via the reaction chamber, and a conduit connected at one end to the sacrificial reservoir and an opposed end to both of the two reservoirs; and a connecting conduit connecting one of the two reservoirs to a sacrificial reservoir of a subsequent one of the plurality of cells.

Each of the embodiments A and B may have one or more of the following additional elements in any combination.

Element 1: the first reservoir is downstream of the at least second reservoir relative to a flow of liquid circulating in the main channel toward the flow inducing element. Element 2: the first and the at least second reservoirs are adjacent to one another. Element 3: a first retention burst valve fluidly connected to an upstream end of the first reservoir, a bursting pressure of the first retention burst valve being greater than the pressure differential of the flow inducing element. Element 4: a second retention burst valve fluidly connected to an upstream end of the main channel, the second retention burst valve having a bursting pressure greater than the bursting pressure of the first retention burst valve and lower than the pressure differential generated by the flow inducing element. Element 5: each of the reservoirs contains a liquid different than liquids contained in a remainder of the reservoirs and in the main channel. Element 6: the flow inducing element is a capillary pump. Element 7: the main channel and the reservoirs are defined in a hydrophilic hydraulic layer and wherein the conduit is an air conduit defined in a hydrophobic pneumatic layer disposed on top of the hydrophilic hydraulic layer. Element 8: the hydrophilic hydraulic layer is made of transparent resin and wherein the hydrophobic pneumatic layer is made of polydimethylsiloxane. Element 9: the main channel, the reservoirs, and the conduit are defined in the same hydrophilic layer, the capillary microfluidic circuit further comprising the main channel, the reservoirs, and the conduit, the circuit further comprising a stop valve fluidly separating the downstream end of the first reservoir from the conduit, a stop valve fluidly separating the second reservoir from the conduit, while the conduit connected opposed ends of the reservoirs and defining an air trap. Element 10: the cover is made of polydimethylsiloxane. Element 11: the main channel, the reservoirs, and the conduit are defined in a the same layer, with a hydrophilic capillary microfluidic circuit further having the main channel, the reservoirs, and a hydrophobic conduit connecting a first reservoir and a second reservoir by opposed ends and the conduit defining air traps. Element 12: the cover is made of polydimethylsiloxane. Element 13: the reservoirs include more than eight reservoirs. Element 14: a first set of retention valves disposed downstream of the vents and upstream of the upstream ends of the reservoirs, retention valves of the first set of retention valves having a bursting pressure greater than the pressure differential of the flow inducing element. Element 15: the retention valves of the first set are defined by channels fluidly connecting the vents to the reservoirs, at least one of a height or a width of the channels less than that of the reservoirs. Element 16: further comprising a second set of retention valves disposed downstream of the downstream ends of the reservoirs and upstream of the main channel. Element 17: the retention valves of the second set are defined by channels fluidly connecting the main channel to the reservoirs, at least one of a height or a width of the channels less than that of the reservoirs. Element 18: a reaction zone downstream of the main channel and upstream of the flow inducing element. Element 19: the reaction zone is patterned with a probe. Element 20: the conduit further fluidly connects an upstream end of one or more additional reservoirs to the downstream end of the first reservoir via the upstream end of the second reservoir, the one or more additional reservoirs being upstream of the second reservoir. Element 21: a number of the cells is ten. Element 22: the reaction chamber is a serpentine conduit. Element 23: the flow inducing element is a capillary pump. Element 24: a first set of retention valves disposed upstream of upstream ends of the reservoirs, retention valves of the first set of retention valves having a bursting pressure greater than the pressure differential of the flow inducing element. Element 25: a second set of retention valves disposed downstream of downstream ends of the reservoirs and upstream of the main channel. Element 26: the retention valves of the second set are defined by channels fluidly connecting the main channel to the reservoirs, at least one of a height or a width of the channels less than that of the reservoirs.

C. A method of operating a microfluidic circuit, comprising: using capillary action to direct a fluid through a main channel from an inlet thereof toward a flow inducing element; draining a first reservoir into the main channel using the flow inducing element; once the first reservoir is drained into the main channel, linking the first reservoir to a second reservoir; and subsequently draining the second reservoir into the main channel using the flow inducing element.

The embodiment C may have one or more of the following additional elements in any combination.

Element 30: linking the first reservoir to the second reservoir of the reservoirs includes linking a downstream end of the first reservoir to an upstream end of the second reservoir. Element 31: filling the reservoirs via vents connected to the reservoirs. Element 32: draining the first reservoir with the flow inducing element includes exerting a pressure differential with the flow inducing element being greater than a bursting pressure of a retention burst valve of the first reservoir. Element 33: linking the first reservoir to the second reservoir includes linking the first reservoir to both of the second reservoir and a third reservoir, drawing the second reservoir including drawing simultaneously the second reservoir and the third reservoir. Element 34: mixing liquids contained respectively in the second reservoir and the third reservoir in a mixing channel. Element 35: temporarily containing the mixed liquids in a reaction chamber.

Element 36: emptying a sacrificial reservoir via the flow inducing element before draining the first reservoir. Element 37: wherein linking the first reservoir to a second reservoir includes connecting the second reservoir to ambient air via a conduit. Element 38: wherein draining the second reservoir via the main channel includes exerting a pressure on the second reservoir being greater than a pressure differential of the flow inducing element. Element 39: wherein draining the first reservoir with the flow inducing element includes draining the first reservoir with a capillary pump. Element 40: draining the main channel with the flow inducing element after all of the reservoirs have been drained by the flow inducing element. Element 41: wherein directing the fluid through the main channel with the flow inducing element includes creating a pressure differential in the main channel with the flow inducing element. Element 42: wherein creating the pressure differential includes creating a suction pressure to draw the liquid toward the flow inducing element. Element 43: wherein creating the pressure differential includes creating a positive pressure to push the liquid away from the flow inducing element. Element 44: wherein creating the positive pressure includes pushing the liquid with air.

It is understood that herein the expressions "interconnecting", "linking", "communicating" means that a fluid communication is created.

The above description is meant to be exemplary only, and one skilled in the art will recognize that changes may be made to the embodiments described without departing from the scope of the invention disclosed. For example, although 3D-printing is described herein as one particular method for creation of the various layers, elements and chips, it is to be understood that other additive manufacturing processes can also be used. Still other modifications which fall within the scope of the present invention will be apparent to those skilled in the art, in light of a review of this disclosure, and such modifications are intended to fall within the appended claims.

The invention claimed is:

1. A capillary microfluidic circuit comprising:
   a main channel communicating with a flow inducing element configured for generating a pressure differential in the main channel to draw one or more liquids into the main channel, the main channel having intermediary inlets distributed along the main channel;
   reservoirs for containing the one or more liquids prior to being drawn into the main channel, the reservoirs including a first reservoir and at least a second reservoir, each of the reservoirs having an upstream end connected to an inlet for filling the reservoirs with the one or more liquids and a downstream end, the downstream end of each of the reservoirs being connected to the intermediary inlets of the main channel, the first reservoir having a vent at the upstream end; and
   a conduit disposed between the first reservoir and the at least second reservoir, the conduit extending from the downstream end of the first reservoir with the upstream end of the at least second reservoir, the conduit defining a gas passage interconnecting the downstream end of the first reservoir to the upstream end of the at least second reservoir independently of the main channel.

2. The capillary microfluidic circuit of claim 1, further comprising a first retention burst valve fluidly connected to an upstream end of the first reservoir, a bursting pressure of the first retention burst valve being greater than the pressure differential of the flow inducing element, and further comprising a second retention burst valve fluidly connected to an upstream end of the main channel, the second retention burst valve having a bursting pressure greater than the bursting pressure of the first retention burst valve and lower than the pressure differential generated by the flow inducing element.

3. The capillary microfluidic circuit of claim 1, wherein each of the reservoirs contains a liquid different than liquids contained in a remainder of the reservoirs and in the main channel.

4. The capillary microfluidic circuit of claim 1, wherein the flow inducing element is a capillary pump.

5. The capillary microfluidic circuit of claim 3, wherein the main channel and the reservoirs are defined in a hydrophilic hydraulic layer and wherein the conduit is an air conduit defined in a hydrophobic pneumatic layer disposed on top of the hydrophilic hydraulic layer.

6. The capillary microfluidic circuit of claim 1, the capillary microfluidic circuit comprising a stop valve fluidly separating the downstream end of the first reservoir from the conduit, a stop valve fluidly separating the second reservoir from the conduit, the conduit connecting opposed ends of the reservoirs and defining an air trap.

7. The capillary microfluidic circuit of claim 6, where the cover is made of polydimethylsiloxane.

8. The capillary microfluidic circuit of claim 1, comprising a sacrificial reservoir configured for containing a sacrificial liquid, the sacrificial reservoir connected to the main channel.

9. The capillary microfluidic circuit of claim 8, comprising a sacrificial conduit connected at one end to the sacrificial reservoir and having an opposed end connected to the reservoirs.

10. The capillary microfluidic circuit of claim 1, further comprising a first set of retention valves disposed downstream of the vents and upstream of the upstream ends of the reservoirs, retention valves of the first set of retention valves having a bursting pressure greater than the pressure differential of the flow inducing element, wherein the retention valves of the first set are defined by channels fluidly connecting the vents to the reservoirs, at least one of a height or a width of the channels less than that of the reservoirs.

11. The capillary microfluidic circuit of claim 10, further comprising a second set of retention valves disposed downstream of the downstream ends of the reservoirs and upstream of the main channel, the retention valves of the second set defined by channels fluidly connecting the main channel to the reservoirs, at least one of a height or a width of the channels less than that of the reservoirs.

12. The capillary microfluidic circuit of claim 8, further comprising a reaction zone downstream of the main channel and upstream of the flow inducing element, the reaction zone is patterned with a probe, the sacrificial reservoir connected to the main channel upstream of the reaction zone.

13. The capillary microfluidic circuit of claim 1, wherein the conduit further fluidly connects an upstream end of one or more additional reservoirs to the downstream end of the first reservoir via the upstream end of the second reservoir, the one or more additional reservoirs being upstream of the second reservoir.

14. The capillary microfluidic circuit of claim 1, comprising a first retention burst valve at an intersection between the downstream end of the first reservoir and the conduit, a second retention burst valve at an intersection between the upstream end of the at least second reservoir and the conduit.

15. The capillary microfluidic circuit of claim 14, comprising a stop valve between the first reservoir and the main channel.

* * * * *